(12) United States Patent
Meijer et al.

(10) Patent No.: US 9,435,001 B2
(45) Date of Patent: Sep. 6, 2016

(54) DETECTION METHOD FOR CERVICAL HPVS

(75) Inventors: Christophorus Joannes Lambertus Maria Meijer, Leiden (NL); Petrus Josephus Ferdinandus Snijders, Amstelveen (NL)

(73) Assignee: SELF-SCREEN B.V., Amsterdam (NL)

(*) Notice: Subject to any disclaimer, the term of this patent is extended or adjusted under 35 U.S.C. 154(b) by 668 days.

(21) Appl. No.: 12/741,018

(22) PCT Filed: Nov. 1, 2007

(86) PCT No.: PCT/NL2007/050526
§ 371 (c)(1),
(2), (4) Date: Aug. 4, 2010

(87) PCT Pub. No.: WO2009/057993
PCT Pub. Date: May 7, 2009

(65) Prior Publication Data
US 2010/0304362 A1  Dec. 2, 2010

(51) Int. Cl.
C12Q 1/70 (2006.01)
C07H 21/04 (2006.01)
A61K 45/06 (2006.01)

(52) U.S. Cl.
CPC ........... *C12Q 1/708* (2013.01); *C12Q 2600/16* (2013.01)

(58) Field of Classification Search
CPC ... A61K 45/06; A61K 31/519; C07D 487/04
See application file for complete search history.

(56) References Cited

U.S. PATENT DOCUMENTS

| | | | |
|---|---|---|---|
| 7,354,719 B2* | 4/2008 | Norman et al. | 435/6.14 |
| 7,682,792 B2* | 3/2010 | Norman et al. | 435/6.12 |
| 8,026,066 B2* | 9/2011 | Norman et al. | 435/6.1 |
| 8,124,334 B2* | 2/2012 | Donegan et al. | 435/6.1 |
| 8,334,098 B2* | 12/2012 | Norman et al. | 435/6.1 |
| 2003/0165821 A1 | 9/2003 | Van Doorn et al. | |
| 2005/0260561 A1* | 11/2005 | Meijer et al. | 435/5 |

FOREIGN PATENT DOCUMENTS

| | | |
|---|---|---|
| EP | 1 818 416 | 8/2007 |
| WO | WO-03/019143 | 3/2003 |
| WO | WO-03/057914 | 7/2003 |
| WO | WO-2004/031416 | 4/2004 |
| WO | WO2005/064020 A1 * | 7/2005 ... C12Q 1/68 |
| WO | WO-2006/038753 | 4/2006 |
| WO | WO-2006/094238 | 9/2006 |

OTHER PUBLICATIONS

Yoneta et al. (British Journal of Dermatology, 2000, vol. 143, p. 604-608).*
de Roda Husman et al. (Journal of General Virology, 1995, vol. 76, p. 1057-1062).*
Gheit et al., Journal of Clinical Microbiology (2006) 44(6):2025-2031.
International Search Report for PCT/NL2007/050526, mailed on Feb. 26, 2008, 5 pages.
Josefsson et al., Journal of Clinical Microbiology (1999) 37(3):490-496.
Karlsen et al., Journal of Clinical Microbiology (1996) 34(9):2095-2100.
Kleter et al., American Journal of Pathology (1998) 153(6):1731-1739.
Kleter et al., Journal of Clinical Microbiology (1999) 37(8):2508-2517.
Peitsaro et al., Journal of Clinical Microbiology (2002) 40(3):886-891.
Tucker et al., Molecular Diagnosis (2001) 6:39-47.
Van Den Brule et al., Journal of Clinical Microbiology (2002) 40(3):779-787.
Walboomers et al., Journal of Pathology (1999) 189:12-19.

* cited by examiner

*Primary Examiner* — Agnieszka Boesen
(74) *Attorney, Agent, or Firm* — Morrison & Foerster LLP

(57) ABSTRACT

The invention describes a consensus PCR based method (i.e. HRE7-PCR) for the simultaneous detection of 14 Human Papilloma Virus types (i.e. HPV 16, 18, 31, 33, 35, 39, 45, 51, 52, 56, 58, 59, 66, and 68) that are classified as (probably) high-risk, relating to the causation of cervical cancer) and a candidate hrHPV type (i.e. HPV 67) using sets of 6 overlapping forward primers and 9 overlapping backward primers that together amplify a fragment of about (215) to (245) base pairs of the E7 open reading frame of these hrHPV types. For the detection of reaction products an EIA format can be used with the aid of a cocktail of type-specific oligoprobes as exemplified herein. Furthermore, we have developed a method for an efficient typing of these (15) HPVs that is compatible with the method for detection. This RLB typing system involves hybridization of PCR products with immobilized type-specific oligoprobes.

3 Claims, 3 Drawing Sheets

Figure 1. Primer sequences of HRE7-PCR

Forward primers (5'-3'):

gacctctactgttatgagcaatt
gacctatactgctatgagcaatt
gaccttgtatgtcacgagcaatt
gaccttttgtgttacgagcaatt
gctacgagcaatttgacagctc
cagaggatgaggatgaggatgaa Backward primers (5'-3'):

tgagaacagatggggcacaca
gtagaacagttggggcacacg
tgcacaggtagggcacacaat
ggggcacactattccaaatgt
gggcacacaacttgtaatg
tgggacacactattcctagtg
tgcacacaacggacacacaaa
gttcgcacaacacgggcaaac
cgcagagtgggcacgttactg Figure 2. EIA probe sequences for HRE7-PCR

| HPV type | EIA probe sequence (5'-3') |
|---|---|
| 16 | Gcacaaccgaagcgtagagtcacacttgc |
| 18 | Aaatgttgatgattaactccatctatt |
| 31 | Cacacaaacgaagtgtagacttacactga |
| 33 | Atctggccggtccaagccttcatcct |
| 35 | Tagtgtcgcctcacatttacaacaggac |
| 39 | Tgtattgtgtgacgctgtggttcatc |
| 45 | Agttgtgcatgactaactccatctgct |
| 51 | Cacttgaacacctgcaacacggagcttcaa |
| 52 | Tgcatagccgtagtgtgctatcacaac |
| 56 | Caaacttacactcacaacaaggtacgtgtat |
| 58 | Cccgtccaagcctatttcatcctcgt |
| 59 | Cagctcgtctagctagtagcaaaggatg |
| 66 | Ccaactcacacttacaacaaggtacgtgaat |
| 67 | Aagtgcactcacagatgttacacacagta |
| 68 | Tgaattgtgtgacgctgttgttcgtc |

Figure 3: Sequence of RLB probes for typing of HRE7-PCR products

| HPV type | RLB probe sequence (5'-3') |
|---|---|
| 16 | Gcgtagagtcacacttgc |
| 18 | Aaatgttgatgattaactcca |
| 31 | Cacaaacgaagtgtagactt |
| 33 | Ggtccaagccttcatcct |
| 35 | Gtcgcctcacatttacaa |
| 39 | Gttgatgttggtgattaact |
| 45 | Ttgtgcatgactaactccat |
| 51 | Gaacacctgcaacacgga |
| 52 | Gccgtagtgtgctatcac |
| 56 | Ttacactcacaacaaggtac |
| 58 | Cgaaccgtggtgccaca |
| 59 | Cgtctagctagtagcaaag |
| 66 | Actcacacttacaccaaggt |
| 67 | Gtgcactcacagatgttac |
| 68 | Tgatgttggtggtgattaac |

SEQUENCE LISTING

```
<160> NUMBER OF SEQ ID NOS: 45

<210> SEQ ID NO 1
<211> LENGTH: 23
<212> TYPE: DNA
<213> ORGANISM: Artificial Sequence
<220> FEATURE:
<223> OTHER INFORMATION: forward primer of HRE7-PCR

<400> SEQUENCE: 1
gacctctact gttatgagca att                                              23

<210> SEQ ID NO 2
<211> LENGTH: 23
<212> TYPE: DNA
<213> ORGANISM: Artificial Sequence
<220> FEATURE:
<223> OTHER INFORMATION: forward primer of HRE7-PCR

<400> SEQUENCE: 2
gacctatact gctatgagca att                                              23

<210> SEQ ID NO 3
<211> LENGTH: 23
<212> TYPE: DNA
<213> ORGANISM: Artificial Sequence
<220> FEATURE:
<223> OTHER INFORMATION: forward primer of HRE7-PCR

<400> SEQUENCE: 3
gaccttgtat gtcacgagca att                                              23

<210> SEQ ID NO 4
<211> LENGTH: 23
<212> TYPE: DNA
<213> ORGANISM: Artificial Sequence
<220> FEATURE:
<223> OTHER INFORMATION: forward primer of HRE7-PCR

<400> SEQUENCE: 4
gaccttttgt gttacgagca att                                              23

<210> SEQ ID NO 5
<211> LENGTH: 22
<212> TYPE: DNA
<213> ORGANISM: Artificial Sequence
<220> FEATURE:
<223> OTHER INFORMATION: forward primer of HRE7-PCR

<400> SEQUENCE: 5
gctacgagca atttgacagc tc                                               22
```

<210> SEQ ID NO 6
<211> LENGTH: 23
<212> TYPE: DNA
<213> ORGANISM: Artificial Sequence
<220> FEATURE:
<223> OTHER INFORMATION: forward primer of HRE7-PCR

<400> SEQUENCE: 6
cagaggatga ggatgaggat gaa                                              23

<210> SEQ ID NO 7
<211> LENGTH: 21
<212> TYPE: DNA
<213> ORGANISM: Artificial Sequence
<220> FEATURE:
<223> OTHER INFORMATION: backward primer of HRE7-PCR

<400> SEQUENCE: 7
tgagaacaga tgggcacac a                                                 21

<210> SEQ ID NO 8
<211> LENGTH: 21
<212> TYPE: DNA
<213> ORGANISM: Artificial Sequence
<220> FEATURE:
<223> OTHER INFORMATION: backward primer of HRE7-PCR

<400> SEQUENCE: 8
gtagaacagt tgggcacac g                                                 21

<210> SEQ ID NO 9
<211> LENGTH: 21
<212> TYPE: DNA
<213> ORGANISM: Artificial Sequence
<220> FEATURE:
<223> OTHER INFORMATION: backward primer of HRE7-PCR

<400> SEQUENCE: 9
tgcacaggta gggcacacaa t                                                21

<210> SEQ ID NO 10
<211> LENGTH: 21
<212> TYPE: DNA
<213> ORGANISM: Artificial Sequence
<220> FEATURE:
<223> OTHER INFORMATION: backward primer of HRE7-PCR

<400> SEQUENCE: 10
ggggcacact attccaaatg t                                                21

<210> SEQ ID NO 11
<211> LENGTH: 19
<212> TYPE: DNA
<213> ORGANISM: Artificial Sequence
<220> FEATURE:
<223> OTHER INFORMATION: backward primer of HRE7-PCR

<400> SEQUENCE: 11
gggcacacaa cttgtaatg                                                   19

<210> SEQ ID NO 12
<211> LENGTH: 21
<212> TYPE: DNA
<213> ORGANISM: Artificial Sequence
<220> FEATURE:
<223> OTHER INFORMATION: backward primer of HRE7-PCR

```
<400> SEQUENCE: 12
tgggacacac tattcctagt g                                              21

<210> SEQ ID NO 13
<211> LENGTH: 21
<212> TYPE: DNA
<213> ORGANISM: Artificial Sequence
<220> FEATURE:
<223> OTHER INFORMATION: backward primer of HRE7-PCR

<400> SEQUENCE: 13
tgcacacaac ggacacacaa a                                              21

<210> SEQ ID NO 14
<211> LENGTH: 21
<212> TYPE: DNA
<213> ORGANISM: Artificial Sequence
<220> FEATURE:
<223> OTHER INFORMATION: backward primer of HRE7-PCR

<400> SEQUENCE: 14
gttcgcacaa cacgggcaaa c                                              21

<210> SEQ ID NO 15
<211> LENGTH: 21
<212> TYPE: DNA
<213> ORGANISM: Artificial Sequence
<220> FEATURE:
<223> OTHER INFORMATION: backward primer of HRE7-PCR

<400> SEQUENCE: 15
cgcagagtgg gcacgttact g                                              21

<210> SEQ ID NO 16
<211> LENGTH: 29
<212> TYPE: DNA
<213> ORGANISM: Artificial Sequence
<220> FEATURE:
<223> OTHER INFORMATION: EIA probe sequence of HRE7-PCR HPV type 16

<400> SEQUENCE: 16
gcacaaccga agcgtagagt cacacttgc                                      29

<210> SEQ ID NO 17
<211> LENGTH: 27
<212> TYPE: DNA
<213> ORGANISM: Artificial Sequence
<220> FEATURE:
<223> OTHER INFORMATION: EIA probe sequence of HRE7-PCR HPV type 18

<400> SEQUENCE: 17
aaatgttgat gattaactcc atctatt                                        27

<210> SEQ ID NO 18
<211> LENGTH: 29
<212> TYPE: DNA
<213> ORGANISM: Artificial Sequence
<220> FEATURE:
<223> OTHER INFORMATION: EIA probe sequence of HRE7-PCR HPV type 31

<400> SEQUENCE: 18
cacacaaacg aagtgtagac ttacactga                                      29

<210> SEQ ID NO 19
```

<211> LENGTH: 26
<212> TYPE: DNA
<213> ORGANISM: Artificial Sequence
<220> FEATURE:
<223> OTHER INFORMATION: EIA probe sequence of HRE7-PCR HPV type 33

<400> SEQUENCE: 19
atctggccgg tccaagcctt catcct                                         26

<210> SEQ ID NO 20
<211> LENGTH: 28
<212> TYPE: DNA
<213> ORGANISM: Artificial Sequence
<220> FEATURE:
<223> OTHER INFORMATION: EIA probe sequence of HRE7-PCR HPV type 35

<400> SEQUENCE: 20
tagtgtcgcc tcacatttac aacaggac                                       28

<210> SEQ ID NO 21
<211> LENGTH: 27
<212> TYPE: DNA
<213> ORGANISM: Artificial Sequence
<220> FEATURE:
<223> OTHER INFORMATION: EIA probe sequence of HRE7-PCR HPV type 39

<400> SEQUENCE: 21
tgtatttgtg tgacgctgtg gttcatc                                        27

<210> SEQ ID NO 22
<211> LENGTH: 27
<212> TYPE: DNA
<213> ORGANISM: Artificial Sequence
<220> FEATURE:
<223> OTHER INFORMATION: EIA probe sequence of HRE7-PCR HPV type 45

<400> SEQUENCE: 22
agttgtgcat gactaactcc atctgct                                        27

<210> SEQ ID NO 23
<211> LENGTH: 30
<212> TYPE: DNA
<213> ORGANISM: Artificial Sequence
<220> FEATURE:
<223> OTHER INFORMATION: EIA probe sequence of HRE7-PCR HPV type 51

<400> SEQUENCE: 23
cacttgaaca cctgcaacac ggagcttcaa                                     30

<210> SEQ ID NO 24
<211> LENGTH: 27
<212> TYPE: DNA
<213> ORGANISM: Artificial Sequence
<220> FEATURE:
<223> OTHER INFORMATION: EIA probe sequence of HRE7-PCR HPV type 52

<400> SEQUENCE: 24
tgcatagccg tagtgtgcta tcacaac                                        27

<210> SEQ ID NO 25
<211> LENGTH: 31
<212> TYPE: DNA
<213> ORGANISM: Artificial Sequence
<220> FEATURE:
<223> OTHER INFORMATION: EIA probe sequence of HRE7-PCR HPV type 56

<400> SEQUENCE: 25
caaacttaca ctcacaacaa ggtacgtgta t                                    31

<210> SEQ ID NO 26
<211> LENGTH: 26
<212> TYPE: DNA
<213> ORGANISM: Artificial Sequence
<220> FEATURE:
<223> OTHER INFORMATION: EIA probe sequence of HRE7-PCR HPV type 58

<400> SEQUENCE: 26
cccgtccaag cctatttcat cctcgt                                          26

<210> SEQ ID NO 27
<211> LENGTH: 28
<212> TYPE: DNA
<213> ORGANISM: Artificial Sequence
<220> FEATURE:
<223> OTHER INFORMATION: EIA probe sequence of HRE7-PCR HPV type 59

<400> SEQUENCE: 27
cagctcgtct agctagtagc aaaggatg                                        28

<210> SEQ ID NO 28
<211> LENGTH: 31
<212> TYPE: DNA
<213> ORGANISM: Artificial Sequence
<220> FEATURE:
<223> OTHER INFORMATION: EIA probe sequence of HRE7-PCR HPV type 66

<400> SEQUENCE: 28
ccaactcaca cttacaacaa ggtacgtgaa t                                    31

<210> SEQ ID NO 29
<211> LENGTH: 29
<212> TYPE: DNA
<213> ORGANISM: Artificial Sequence
<220> FEATURE:
<223> OTHER INFORMATION: EIA probe sequence of HRE7-PCR HPV type 67

<400> SEQUENCE: 29
aagtgcactc acagatgtta cacacagta                                       29

<210> SEQ ID NO 30
<211> LENGTH: 26
<212> TYPE: DNA
<213> ORGANISM: Artificial Sequence
<220> FEATURE:
<223> OTHER INFORMATION: EIA probe sequence of HRE7-PCR HPV type 68

<400> SEQUENCE: 30
tgaattgtgt gacgctgttg ttcgtc                                          26

<210> SEQ ID NO 31
<211> LENGTH: 18
<212> TYPE: DNA
<213> ORGANISM: Artificial Sequence
<220> FEATURE:
<223> OTHER INFORMATION: RLB probe sequence for HRE7-PCR HPV type 16

<400> SEQUENCE: 31
gcgtagagtc acacttgc                                                   18

<210> SEQ ID NO 32
<211> LENGTH: 21
<212> TYPE: DNA

```
<213> ORGANISM: Artificial Sequence
<220> FEATURE:
<223> OTHER INFORMATION: RLB probe sequence for HRE7-PCR HPV type 18

<400> SEQUENCE: 32
aaatgttgat gattaactcc a                                              21

<210> SEQ ID NO 33
<211> LENGTH: 20
<212> TYPE: DNA
<213> ORGANISM: Artificial Sequence
<220> FEATURE:
<223> OTHER INFORMATION: RLB probe sequence for HRE7-PCR HPV type 31

<400> SEQUENCE: 33
cacaaacgaa gtgtagactt                                                20

<210> SEQ ID NO 34
<211> LENGTH: 18
<212> TYPE: DNA
<213> ORGANISM: Artificial Sequence
<220> FEATURE:
<223> OTHER INFORMATION: RLB probe sequence for HRE7-PCR HPV type 33

<400> SEQUENCE: 34
ggtccaagcc ttcatcct                                                  18

<210> SEQ ID NO 35
<211> LENGTH: 18
<212> TYPE: DNA
<213> ORGANISM: Artificial Sequence
<220> FEATURE:
<223> OTHER INFORMATION: RLB probe sequence for HRE7-PCR HPV type 35

<400> SEQUENCE: 35
gtcgcctcac atttacaa                                                  18

<210> SEQ ID NO 36
<211> LENGTH: 20
<212> TYPE: DNA
<213> ORGANISM: Artificial Sequence
<220> FEATURE:
<223> OTHER INFORMATION: RLB probe sequence for HRE7-PCR HPV type 39

<400> SEQUENCE: 36
gttgatgttg gtgattaact                                                20

<210> SEQ ID NO 37
<211> LENGTH: 20
<212> TYPE: DNA
<213> ORGANISM: Artificial Sequence
<220> FEATURE:
<223> OTHER INFORMATION: RLB probe sequence for HRE7-PCR HPV type 45

<400> SEQUENCE: 37
ttgtgcatga ctaactccat                                                20

<210> SEQ ID NO 38
<211> LENGTH: 18
<212> TYPE: DNA
<213> ORGANISM: Artificial Sequence
<220> FEATURE:
<223> OTHER INFORMATION: RLB probe sequence for HRE7-PCR HPV type 51

<400> SEQUENCE: 38
gaacacctgc aacacgga                                                  18
```

<210> SEQ ID NO 39
<211> LENGTH: 18
<212> TYPE: DNA
<213> ORGANISM: Artificial Sequence
<220> FEATURE:
<223> OTHER INFORMATION: RLB probe sequence for HRE7-PCR HPV type 52

<400> SEQUENCE: 39
gccgtagtgt gctatcac                                                 18

<210> SEQ ID NO 40
<211> LENGTH: 20
<212> TYPE: DNA
<213> ORGANISM: Artificial Sequence
<220> FEATURE:
<223> OTHER INFORMATION: RLB probe sequence for HRE7-PCR HPV type 56

<400> SEQUENCE: 40
ttacactcac aacaaggtac                                               20

<210> SEQ ID NO 41
<211> LENGTH: 17
<212> TYPE: DNA
<213> ORGANISM: Artificial Sequence
<220> FEATURE:
<223> OTHER INFORMATION: RLB probe sequence for HRE7-PCR HPV type 58

<400> SEQUENCE: 41
cgaaccgtgg tgccaca                                                  17

<210> SEQ ID NO 42
<211> LENGTH: 19
<212> TYPE: DNA
<213> ORGANISM: Artificial Sequence
<220> FEATURE:
<223> OTHER INFORMATION: RLB probe sequence for HRE7-PCR HPV type 59

<400> SEQUENCE: 42
cgtctagcta gtagcaaag                                                19

<210> SEQ ID NO 43
<211> LENGTH: 20
<212> TYPE: DNA
<213> ORGANISM: Artificial Sequence
<220> FEATURE:
<223> OTHER INFORMATION: RLB probe sequence for HRE7-PCR HPV type 66

<400> SEQUENCE: 43
actcacactt acaccaaggt                                               20

<210> SEQ ID NO 44
<211> LENGTH: 19
<212> TYPE: DNA
<213> ORGANISM: Artificial Sequence
<220> FEATURE:
<223> OTHER INFORMATION: RLB probe sequence for HRE7-PCR HPV type 67

<400> SEQUENCE: 44
gtgcactcac agatgttac                                                19

<210> SEQ ID NO 45
<211> LENGTH: 20
<212> TYPE: DNA
<213> ORGANISM: Artificial Sequence
<220> FEATURE:

-continued

<223> OTHER INFORMATION: RLB probe sequence for HRE7-PCR HPV type 68

<400> SEQUENCE: 45
tgatgttggt ggtgattaac   20

DETECTION METHOD FOR CERVICAL HPVS

CROSS-REFERENCE TO RELATED APPLICATIONS

This application is the national phase of PCT application PCT/NL2007/050526 having an international filing date of 1 Nov. 2007. The contents of the above patent application is incorporated by reference herein in its entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 3136320090000Seqlist.txt | Jul. 26, 2010 | 9,209 bytes |

The invention relates to the detection of human papillomavirus (HPV) in cervical cancers, more specifically a detection based on nucleotide sequences of high-risk cervical HPVs.

The causal relationship between high-risk human papillomavirus (hrHPV) infection and cervical cancer has become evident from epidemiological and functional studies (Zur Hausen, 2002, Nat. Rev. Cancer 2:342-350; Bosch et al., 2002, J. Clin. Pathol. 55:144-265). The HPV genome is an 8 kb, circular, double stranded DNA comprising 8 genes, all encoded on the same strand. As many as 200 different HPV types have been identified in humans (Burd, E. M. 2003, Clin Microbiol Rev. 16:1-17); of these approximately 40 types have been found capable of infecting the genital tract. Based on a pooled analysis of large world-wide case-control studies, an epidemiological classification of hrHPV types was made, indicating that 15 HPV types (HPV 16, 18, 31, 33, 35, 39, 45, 51, 52, 56, 58, 59, 68, 73 and 82) can be classified as high-risk and another 3 (HPV 26, 53 and 66) as probably high-risk (Munoz et al., 2003, N. Eng. J. Med. 348:518-527). HrHPVs have been detected in up to 99.7% of cervical squamous cell carcinomas (SCCs) (Walboomers et al., 1999, J. Pathol. 189:12-19) and at least 94% of cervical adeno- and adenosquamous carcinomas (Zielinsky et al., 2003, J. Pathol. 201:535-543).

Cervical cancer accounts for nearly 10% of all female cancers and is a leading cause of cancer among women in developing countries (Franco, E. L. et al., 2001, Can Med Assoc J 164: 1017-25). The regions with the highest incidence of the disease are generally those with the greatest mortality and include Central America, Africa, and the Caribbean (Ferlay, J. et al., 1998. IARC CancerBase no. 3. Lyon: IARC Press.). Incidence in Europe and North America has declined precipitously over the past 50 years, possibly due to the advent of routine screening by Papanicolaou (Pap) smear testing (reviewed in Franco et al., ibid). Cervical cancer is one of the most preventable cancers, with survival being directly related to the stage of the disease at diagnosis. The 5-year survival rate is 88% for women having initial diagnosis of localized disease as opposed to 13% for women diagnosed with distant disease (Report of the Gynecologic Cancers Progress Review Group, November 2001, National Cancer Institute). More than 50% of women diagnosed with cervical cancer in the U.S. have not had a Pap smear in the past three years (Wright, T. C. et al., 2000, JAMA 283: 81-6).

Pap screening remains the predominant mode of detecting cancerous and precancerous cervical lesions; more than 50 million women undergo Pap screening each year in the U.S. (Wright, T. C. et al., 2002, JAMA 287: 2120-29). Despite its widespread use, Pap smear testing is only partially effective and shows a substantial degree of both false-negative and false-positive test results; based on some estimates the sensitivity of conventional Pap smear testing varies from 50-60% (Lorincz, A. T. and Richart, R. M., 2003, Arch Pathol Lab Med 127: 959-68; Nanda, K. et al., 2000. Ann Intern Med 132:810; Fahey M T, et al. 1995, Am J Epidemiol. 141: 680-9; Myers E R, McCrory D C, Subramanian S, et al. 2000, Obstet Gynecol 96: 645-52.) to 70-80% (Clavel, C. et al., 2001. Br J Cancer 84: 1616). Recent innovations in cytological screening and sampling, such as liquid-based tests, have improved the sensitivity of these methods to 75-95% (Lorincz, A. T. et al. ibid; Nanda, K. et al., ibid. Hutchinson M L, Zahniser D J, Sherman M E, et al. 1999 Cancer. 87: 48-55). Nonetheless, even these improved methods fail to detect a significant portion of abnormal, and often precancerous, cells. Addition of hrHPV DNA testing to the Pap test is likely to improve the efficacy of cervical screening programs particularly because of its high negative predictive value for cervical carcinoma and closest precursor lesion (i.e. lesions ≥CIN3). Moreover, some authorities are calling for HPV DNA screening for use in conjunction with, or in some cases, in lieu of, conventional cytological methods (Wright, T. C. and Schiffman, M., 2003. N. Engl. J. Med. 348:489-90).

The HPV tests that are currently most widely applied are based on two principles. The first, as used in the FDA approved Hybrid Capture 2 (hc2) assay, involves hybridization of HPV target DNA with a cocktail of full-length HPV type-specific RNAs, followed by capturing DNA/RNA hybrids to a solid phase. Subsequently, signal amplification is achieved by binding of hybrids to multiple conjugated antibodies that specifically recognize DNA/RNA hybrids. The second principle involves PCR amplification of HPV target DNA directed by so-called consensus or general primers that bind to highly conserved regions within E1 or L1 open reading frames of all relevant genital hrHPV genotypes. Several read out systems have been described for the latter assays, but enzyme immuno-assays (e.g. EIA, DEIA) using type-specific oligoprobes (either individually or in a cocktail (Jacobs et al., 1997, J Clin Microbiol 35:791-795; Meter et al., 1998, Am J Pathol: 153:1731-1739) or reverse line blot assays (e.g. LiPA, RLB (van den Brule et al., 2002, J Clin Microbiol 40:779-787; Meter et al., 1999, J Clin Microbiol; 37:2508-2517; Gravitt et al., 1998, J Clin Microbiol 36:3020-3027) are nowadays most commonly used. Amongst the HPV consensus PCR systems, the L1-based PGMY-PCR (redesigned from MY11/09-PCR primers (Gravitt et al., 2000, J Clin Microbiol 38:357-361), GP5+/6+-PCR (van den Brule et al., 2002, J Clin Microbiol 40:779-787) and SPF10-LiPA (Meter et al., 1999, J Clin Microbiol 37:2508-2517) are currently most frequently applied. More recently, a novel L1-based consensus PCR system, the Roche AMPLICOR® HPV Test, was launched, which is capable of detecting 13 hrHPV types.

All currently available hrHPV testing systems have some intrinsic drawbacks that are not easily to be resolved by adapting assay or read-out conditions. Particular in case hrHPV testing would be envisaged as a primary screening tool, with reflex cytology being applied on hrHPV positive cases, these drawbacks may have substantial negative consequences for either the positive or negative predictive values of tests for high-grade premalignant cervical lesions and cervical cancer. This is particularly relevant in case self-sampled vaginal material would be used for screening purposes. This material is not suitable for a reliable cytological assessment but highly representative for the hrHPV status of the cervix.

A. The hc2 method shows a certain degree of cross-reactivity with HPV types, including low risk HPV types, which are not represented in the probe mixture (Castle et al., Cancer Epidemiol Biomarkers Prev. 2002: 11: 1394-1399). This has a negative impact on the specificity of this assay for risk assessment of cervical cancer.

B. On the other hand, the various PCR-based systems display different analytical sensitivities for hrHPVs, which in practice give rise to different specificities for high-grade pre-malignant cervical lesions and cervical cancer. The latter is owing to the fact that many hrHPV infections, particularly those with a low viral load, reflect transient infections that are clinically irrelevant, whereas infections associated with high-grade cervical disease generally are characterized by increased viral loads (Snijders et al., J Pathol. 2003: 201:1-6; van Duin et al., Int J Cancer 2002:98:590-595; Schlecht et al Int J cancer 2003: 103: 519-524.). Thus, analytical test sensitivity (i.e. sensitivity to detect hrHPV) is not a sufficient requirement for use in clinical and screening practice. Tests that are too sensitive in detecting hrHPV suffer from a reduced specificity for high-grade cervical disease because of an increased detection of transient hrHPV infections characterised by low viral loads. As a consequence, whereas most consensus hrHPV DNA assays show similar sensitivities for high-grade premalignant cervical lesions and cervical cancer, specificity values can vary markedly. Currently, the GP5+/6+ PCR and hc2 assays are the only two tests displaying an optimal balance between sensitivity and specificity for high-grade premalignant cervical lesions and cervical carcinoma and therefore can be considered clinically validated (Lorincz and Richart, Arch Pathol Lab Med 2003: 127:959-968; Bulk et al. Int J Cancer 2007: 121: 361-367) These assays have a similar sensitivity and specificity when used for the detection of ≥CIN2 lesions (Hesselink et al. J Clin Microbiol 2006:44: 3680-3685).

C. Particularly in high-grade premalignant cervical lesions and cervical carcinomas the hrHPV genome is often integrated into the genome of the host cell. Since this phenomenon is often accompanied with interruption of the viral genome in a region that may extend from the E1 to the L1 open reading frame, this may have consequences for PCR-mediated amplification of viral DNA in these regions. Indeed, there are indications that integration prevents detection of viral DNA by E1 and/or L1-based PCR assays in about 4% of cervical SCCs (Walboomers et al., 1999, J Pathol 189: 12-19), 5% of all HSIL, 6% of cervical adenocarcinoma in situ lesions, and 10% of cervical adenocarcinomas (Zielinski et al., 2003, J Pathol 201:535-543). These false-negative scores for cervical carcinomas and high-grade precursor lesions of E1 and L1-based PCR methods are unacceptably high in case hrHPV testing would be envisaged as a primary screening tool, with reflex cytology being applied on hrHPV positive cases.

Thus, there is still need for an improved detection system of hrHPVs.

SUMMARY OF THE INVENTION

In order to overcome these difficulties the inventors have now found a method for the simultaneous detection of 14 hrHPV types (i.e. HPV type 16, 18, 31, 33, 35, 39, 45, 51, 52, 56, 58, 59, 66 and 68) and a candidate hrHPV type (HPV 67), that shows a similar specificity for high-grade cervical lesions as the GP5+/6+-PCR but which is not influenced by viral DNA integration. Furthermore, and in an additional aspect of the invention, the inventors have found a method for an efficient typing system for HPV types belonging to the above mentioned hrHPV types that is compatible with the method for detection.

A method for the detection of hrHPVs according to the present invention comprises the steps of providing a sample suspected of harbouring hrHPVs, providing a plurality of forward and backward primers collectively substantially complementary to DNA of said hrHPVs, performing a reaction to amplify DNA derived from the said sample using said plurality of primers; and detecting DNA amplification products from hrHPV types by hybridising the reaction products of the said DNA amplification reaction to a plurality of specific hrHPV probes.

In an additional aspect, the invention provides a method for typing of a hrHPV comprising the steps of providing DNA amplification products by amplifying DNA of hrHPV using a plurality of forward and backward primers, and detecting DNA amplification products from one or more hrHPV types by hybridising the said amplification products to at least one specific hrHPV probe that is substantially complementary to the DNA of at least one but not all hrHPV types.

In a further aspect, the invention provides a set of forward and backward amplification primers for the amplification of hrHPV-DNA.

In yet another aspect, the invention provides type-specific oligonucleotide probes for the type-specific or selective detection of individual hrHPV-types.

DESCRIPTION OF THE FIGURES

FIG. 1 shows a set of forward (SEQ ID NOS:1-6) and backward (SEQ ID NOS:7-15) primers used in the PCR amplification of HRE7 from hrHPV FIG. 2 shows the sequences of EIA probes (SEQ ID NOS:16-30) for detection of HRE7-PCR products.

FIG. 3 shows the sequences of RLB probes (SEQ ID NOS:31-45) for typing of HRE7-PCR products.

DETAILED DESCRIPTION OF THE INVENTION

A "complement" or "complementary sequence" is a sequence of nucleotides which forms a hydrogen-bonded duplex with another sequence of nucleotides according to Watson-Crick base-paring rules. For example, the complementary base sequence for 5'-AAGGCT-3' is 3'-TTCCGA-5'.

"Expression" refers to the transcription of a gene into structural RNA (rRNA, tRNA) or messenger RNA (mRNA) and, if applicable, subsequent translation into a protein.

Polynucleotides are "heterologous" to one another if they do not naturally occur together in the same organism. A polynucleotide is heterologous to an organism if it does not naturally occur in its particular form and arrangement in that organism.

Polynucleotides have "homologous" sequences if the sequence of nucleotides in the two sequences is the same when aligned for maximum correspondence as described herein. Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence homology" for polynucleotides, such as 50, 60, 70, 80, 90, 95, 98, 99 or 100 percent sequence homology may be determined by comparing two optimally aligned sequences over a comparison window, wherein the portion of the polynucleotide sequence in the comparison window may include additions or deletions (i.e. gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by inspection. Readily available sequence comparison and multiple sequence alignment algorithms are, respectively, the Basic Local Alignment Search Tool (BLAST) (Altschul, S. F. et al. 1990. J. Mol. Biol. 215:403; Altschul, S. F. et al. 1997. Nucleic Acid Res. 25:3389-3402) and ClustalW programs both available on the internet. Other suitable programs include GAP, BESTFIT and FASTA in the Wisconsin Genetics Software Package (Genetics Computer Group (GCG), Madison, Wis., USA).

As used herein, "substantially complementary" means that two nucleic acid sequences have at least about 90%, preferably about 93%, more preferably about 95%, and most preferably about 98%, sequence complementarity to each other. This means that the primers and probes must exhibit sufficient complementarity to their template and target nucleic acid, respectively, to hybridise under stringent conditions. Therefore, the primer sequences as disclosed in this specification need not reflect the exact sequence of the binding region on the template and degenerate primers can be used. A substantially complementary primer sequence is one that has sufficient sequence complementarity to the amplification template to result in primer binding and second-strand synthesis.

The term "hybrid" refers to a double-stranded nucleic acid molecule, or duplex, formed by hydrogen bonding between complementary nucleotides. The terms "hybridise" or "anneal" refer to the process by which single strands of nucleic acid sequences form double-helical segments through hydrogen bonding between complementary nucleotides.

The term "oligonucleotide" refers to a short sequence of nucleotide monomers (usually 6 to 100 nucleotides) joined by phosphorous linkages (e.g., phosphodiester, alkyl and aryl-phosphate, phosphorothioate), or non-phosphorous linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-β-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming stable secondary structures (e.g., stem-and-loop and loop-stem-loop structures).

The term "primer" as used herein refers to an oligonucleotide which is capable of annealing to the amplification target allowing a DNA polymerase to attach thereby serving as a point of initiation of DNA synthesis when placed under conditions in which synthesis of primer extension product which is complementary to a nucleic acid strand is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxy ribonucleotide. The primer must be sufficiently long to prime the synthesis of extension products in the presence of the agent for polymerization. The exact lengths of the primers will depend on many factors, including temperature and source of primer. A "pair of bi-directional primers" as used herein refers to one forward and one reverse primer as commonly used in the art of DNA amplification such as in PCR amplification.

The term "probe" refers to a single-stranded oligonucleotide sequence that will recognize and form a hydrogen-bonded duplex with a complementary sequence in a target nucleic acid sequence analyte or its cDNA derivative.

The terms "stringency" or "stringent hybridization conditions" refer to hybridization conditions that affect the stability of hybrids, e.g., temperature, salt concentration, pH, formamide concentration and the like. These conditions are empirically optimised to maximize specific binding and minimize non-specific binding of primer or probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of a complementary target sequence hybridises to a perfectly matched probe or primer. Typically, stringent conditions will be those in which the salt concentration is less than about 1.0 M Na$^+$ ion, typically about 0.01 to 1.0 M Na$^+$ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1 M NaCl, 1% SDS at 37° C., and a wash in 0.1×SSC at 60° C. Hybridization procedures are well known in the art and are described in e.g. Ausubel et al, Current Protocols in Molecular Biology, John Wiley & Sons Inc., 1994.

A method of the present invention permits the detection, identification and diagnosis of human papillomaviruses belonging to the subgroup of high-risk human papillomaviruses (hrHPV) in cervical and other anogenital cancers that are caused by hrHPV.

Detection of hrHPVs

A method for detection of 14 hrHPV types (i.e. HPV type 16, 18, 31, 33, 35, 39, 45, 51, 52, 56, 58, 59, 66 and 68) and a candidate hrHPV type (HPV 67) (hereinafter indicated as hrHPVs) according to the present invention may be performed on human clinical samples. Preferably, a sample for use in a method of the invention comprises a cervical smear sample of a woman in order to assess her risk of cervical cancer.

Methods of obtaining and preparing such samples for use in the method of the invention are known to those skilled in the art or will be apparent from the present disclosure. For general methods concerning DNA analysis and manipulations see e.g. Molecular Cloning: A Laboratory Manual, 2nd Ed., Vol. 1-3, eds. Sambrook et al. Cold Spring Harbor Laboratory Press (1989) or Current Protocols in Molecular Biology, eds. Ausubel et al., Greene Publishing and Wiley-Interscience, New York (1987) and periodic updates thereof.

Preferably, a method according to the invention is used for the detection of 14 hrHPV types (i.e. HPV type 16, 18, 31, 33, 35, 39, 45, 51, 52, 56, 58, 59, 66 and 68) and a candidate hrHPV type (HPV 67).

It is an advantageous aspect of the invention that members of the subgroup of hrHPVs that are not yet tested for or discovered may suitably be detected by using a method of the present invention.

In the method for detection of hr-HPVs of the present invention a consensus PCR based method is described using sets of 6 forward primers and 9 backward primers, some of which overlap, that together amplify a fragment of about 215 to 245 base pairs of the E7 open reading frame, dependent on the HPV type.

The viral oncogene E7 is important for both the initiation and the maintenance of the transformed phenotype mediated by hrHPV. Factually this means that the E7 open reading frame is always retained in cervical cancer and its precursor stages (Zur Hausen, supra). In addition, it has surprisingly appeared that the E7 region is sufficiently heterogenous amongst the different HPV types to select primer and probe combinations that do not cross-react with other HPV types.

The above-mentioned forward and backward primers match to regions at or in between nucleotide positions 622-644 and 828-847, respectively, of the HPV type 16 genome (GenBank accession number NC 001526) and equivalent positions within the genome of other hrHPV genotypes. The best matching primers in the cocktail have at maximum two mismatches with target sequences of the respective HPV types.

Based on this finding the present invention provides a set of forward and backward primers wherein each individual primer is capable of annealing to the E7 region of one or more hrHPV types. The complete set of 6 forward and 9 backward primers provides a plurality of primers that, when used in concert, are capable of annealing to the E7 DNA of any of the mentioned hrHPVs and of amplifying the defined DNA sequences between and adjacent the positions 622-644 and 828-847 of HPV 16 and equivalent positions within the genome of other hrHPV types.

The strength of the set of primers is their broad specificity with regard to the hrHPV types while maintaining an optimal sensitivity. The sensitivity is optimal because it is high enough to be able to detect real hrHPV infections, while it is low enough not to be triggered by a very low viral load, which is characteristic for transient and clinically irrelevant amounts of hrHPV in the sample. This remarkable combination is achieved by selecting primers that are in most cases not 100% complementary to the target viral sequences, but contain one or two mismatches. Primer sets of the prior art, e.g. the primer sets as disclosed in WO 03/020976, have a high analytical sensitivity for hrHPV and, consequently have a lower specificity for CIN2 or CIN3 lesions (Snijders, P. et al., 2003, J. Pathol. 201:1-6).

The set of forward and backward primers to amplify said region is presented in FIG. 1. It is possible to use somewhat shorter or somewhat longer primers. In the present set of primers of FIG. 1 the backward primers are intentionally shorter than the forward primers in order to equalize the Tm of the primer mixes.

Methods of the invention can in principle be performed by using any nucleic acid amplification method, such as the Polymerase Chain Reaction (PCR; Mullis 1987, U.S. Pat. Nos. 4,683,195, 4,683,202, en 4,800,159) or by using amplification reactions such as Ligase Chain Reaction (LCR; Barany 1991, Proc. Natl. Acad. Sci. USA 88:189-193; EP Appl. No., 320,308), Self-Sustained Sequence Replication (3SR; Guatelli et al., 1990, Proc. Natl. Acad. Sci. USA 87:1874-1878), Strand Displacement Amplification (SDA; U.S. Pat. Nos. 5,270,184, en 5,455,166), Transcriptional Amplification System (TAS; Kwoh et al., Proc. Natl. Acad. Sci. USA 86:1173-1177), Q-Beta Replicase (Lizardi et al., 1988, Bio/Technology 6:1197), Rolling Circle Amplification (RCA; U.S. Pat. No. 5,871,921), Nucleic Acid Sequence Based Amplification (NASBA), Cleavage Fragment Length Polymorphism (U.S. Pat. No. 5,719,028), Isothermal and Chimeric Primer-initiated Amplification of Nucleic Acid (ICAN), Ramification-extension Amplification Method (RAM; U.S. Pat. Nos. 5,719,028 and 5,942,391) or other suitable methods for amplification of DNA.

A preferred embodiment according to the present invention uses a PCR method comprising the primer-initiated amplification of hrHPV-DNA with the set of 6 forward and 9 backward (or reverse) primers of FIG. 1.

In order to amplify the DNA of HPV types with a small number of mismatches with one or more of the amplification primers, an amplification reaction may be performed under conditions of reduced stringency (e.g. a PCR amplification using an annealing temperature of down to 38° C., or the presence of up to 3.5 mM $MgCl_2$). The person skilled in the art will be able to select conditions of suitable stringency.

The detection of the amplification products can in principle be accomplished by any suitable method known in the art. The detection fragments may be directly stained or labelled with radioactive labels, antibodies, luminescent dyes, fluorescent dyes, or enzyme reagents. Direct DNA stains include for example intercalating dyes such as acridine orange, ethidium bromide, ethidium monoazide or Hoechst dyes. Preferably an EIA format can be used with the aid of a cocktail of type-specific oligoprobes as exemplified in FIG. 2. In another preferred embodiment detection takes place by hybridisation with immobilised type-specific oligoprobes (FIG. 3).

Alternatively, the DNA fragments may be detected by incorporation of labelled dNTP bases into the synthesized DNA fragments. Detection labels which may be associated with nucleotide bases include e.g. fluorescein, cyanine dye or BrdUrd.

The present invention preferably involves the detection of the reaction products obtained by the above described DNA amplification reaction on hrHPV DNA by hybridising the reaction products to one or more specific hrHPV probes.

When using a probe-based detection system, a suitable detection procedure for use in the present invention may for example comprise an enzyme immunoassay (EIA) format (Jacobs et al., 1997, J. Clin. Microbiol. 35, 791-795). For performing a detection by manner of the EIA procedure, either the forward or the reverse primer used in the amplification reaction may comprise a capturing group, such as a biotin group for immobilization of hrHPV-DNA PCR amplicons on e.g. a streptavidin coated microtiter plate wells for subsequent EIA detection of hrHPV-amplicons (see below). The skilled person will understand that other groups for immobilization of hrHPV-DNA PCR amplicons in an EIA format may be employed.

Typing of hrHPVs

It has further appeared that the E7 region is sufficiently heterogenous amongst the different HPV types to select primer and probe combinations that do not cross-react with other HPV types.

Therefore, and in another aspect of the invention, the various HPV types belonging to the hrHPV types as listed above may be detected by using a plurality of type-specific hrHPV detection probes that, individually, bind only to the amplicon of one specific high risk type of HPV. Thus, by amplifying the DNA sequence region between the two consensus regions as defined herein, followed by probing for the unique sequences of each individual HPV-type, a method is provided for typing of the various high risk HPVs.

Probes useful for the type-specific detection of the E7 region as disclosed herein are exemplified in FIG. 2 for EIA detection and in FIG. 3 for detection by reverse line blotting (RLB). These type-specific probes preferably bind only to at least a part of the DNA sequence region as amplified between the two consensus regions of a single HPV-type belonging to the group of hrHPVs. Also the complementary sequences of those listed in FIG. 3 may suitably be used as type-specific detection probes in a method of the invention, provided that such a complementary strand is amplified in the amplification reaction employed.

Probes used in a method of typing according to the invention bind selectively to the amplicon of a certain HPV type or types, but not—or only weakly under hybridization conditions of very low stringency—to the amplicon of other HPV types. Accordingly, in one embodiment, the invention can be used to determine the type or types of HPV infecting a patient. This is very significant, as progression to malignant disease (and hence clinical prognosis) is heavily dependent on HPV type. Accordingly, in a typing aspect, the invention provides a method of determining the type(s) of HPV infection in a patient.

In a preferred embodiment of a method for typing of hrHPVs of the present invention a set of 15 different probes (FIG. 3), or the complementary sequences thereof, is used that hybridise to the type-specific sequences in the amplicons derivable from the 15 different hrHPVs.

Suitable detection procedures for use in the typing aspect of present invention may for example comprise immobilization of the amplicons and probing the DNA sequences thereof by e.g. Southern blotting. Other formats may comprise an EIA format as described above (and then preferably the probes of FIG. 2 are used). To facilitate the detection of binding, the type-specific hrHPV probes may comprise a label moiety such as a fluorophore, a chromophore, an enzyme or a radio-label, so as to facilitate monitoring of binding of the probes to the reaction product of the amplification reaction. Such labels are well-known to those skilled in the art and include, for example, fluorescein isothiocyanate (FITC), β-galactosidase, horseradish peroxidase, streptavidin, biotin, digoxigenin, $^{35}$S or $^{125}$I. Other examples will be apparent to those skilled in the art.

Although other methods may be employed, a method of typing according to the invention is preferably performed by hybridisation of PCR products to type-specific probes immobilized to beads or RLB filters, such as recently described for e.g. an L1-based consensus HPV PCR method (van den Brule et al., 2002, J. Clin. Microbiol. 40, 779-787). For this purpose RLB probes are preferably synthesized with a 5' amino group for subsequent immobilization on e.g. carboxyl-coated nylon membranes. The advantage of such a format is the ease of the system and its speed, thus allowing for high throughput sample processing.

A method of typing hrHPVs according to the invention may be performed on fresh sample material as described above (only if such samples would provide sufficient virus DNA). Alternatively, the typing of the hrHPVs according to a method of the invention may be performed directly on amplicons or DNA amplification reaction products obtained by using the DNA amplification reaction as described herein above.

Primers and Probes

In a further aspect, the invention provides a set of forward and backward amplification primers for the amplification of hrHPV-DNA for use in a method of the invention. These primers are preferably oligonucleotide primers with a sequence length of about 8 to about 35, preferably of about 15 to about 30, more preferably of about 18 to about 25 nucleotides. In a most preferred embodiment the forward primer comprises about 22 to 23 nucleotides, while the reverse primer comprises about 19 to 21 nucleotides. Preferably one of the primers is labelled with a group to facilitate the immobilization or staining of one of strands of the double stranded hrHPV amplicons.

The nucleotide sequence of the forward and backward primers of the present invention should be designed to allow the formation of a stable hybrid between the primer and the target DNA at the position of one of the two consensus regions in the E7 region of the hrHPV genome as defined herein. Thereto, the nucleotide sequence of the forward primer is preferably chosen from the group of forward primers presented in FIG. 1. Similarly, the backward or reverse primer is preferably chosen from the group of backward primers presented in FIG. 1. When used in concert, the primers of FIG. 1 will amplify DNA of a corresponding region in the genome of all hrHPVs as defined herein.

The primers have been selected to be "substantially" complementary to the consensus regions present on the different strands of each specific sequence to be amplified. It is possible to use somewhat shorter or somewhat longer primers compared to the sequences of the primers of FIG. 1.

The amplicons comprise regions characterized by common motifs as well as unique sequences between the various hrHPVs.

In another aspect, the invention provides oligonucleotide probes for the type-specific or selective detection of individual HPV-types or subsets of types belonging to hrHPV types. In a preferred embodiment one probe is provided for each HPV type, such probes therefore being type-specific. The present invention discloses two sets of 15 suitable type-specific probe sequences for the type-specific detection of the specific hrHPVs mentioned in FIGS. 2 and 3. Although some mismatches would be allowable it is preferred that the typing probes are perfectly complementary to their respective target sequences. As outlined above, the complementary sequences of those presented in FIGS. 2 and 3 may also be used as type specific probes in methods of the present invention, provided that the amplification reaction allows for the amplification of the complementary DNA fragments. Therefore, when referring to the probes of FIGS. 2 and 3, it is intended that complementary sequences thereof are included.

Type-specific or selective detection probes can be used in a variety of typing procedures. Suitable procedures comprise those whereby the probe-target is immobilized, but also procedures whereby the probes are immobilized may be used. As examples of the latter, both biochip-type of formats, bead formats, but also reverse line blot formats, such as RLB or Line Probe Assays may be used. Depending on the substrate for immobilization and the surface chemistry selected, the skilled person is able to choose a suitable group with which the oligonucleotide probe is labelled for substrate immobilization. In a preferred embodiment this group is an amino-group introduced at the 5'-end of the probe.

The type-specific detection probes are preferably oligonucleotide probes with a sequence length of about 8 to about 35, preferably of about 15 to about 35 nucleotides. For the EIA assay generally longer probes, i.e. about 25 to about 35 nucleotides, preferably about 26 to 31 nucleotides, are preferred. For RLB assays in general shorter probes will suffice, of about 15 to about 22 nucleotides, more preferably about 18 to about 20 nucleotides. The skilled person is aware that the annealing temperature of individual probes within a set of probes that is used in one hybridization reaction may suitable be adjusted by providing balance between G+C content and length of the probe.

In one embodiment the present invention also provides a kit comprising primers and probes for performing a method of the invention. A preferred embodiment of such a kit comprises both the amplification primers as disclosed in FIG. 1 and the type-specific probes, as disclosed in either or both of FIGS. 2 and 3.

The following non-limiting examples illustrate several embodiments of the present invention.

EXAMPLES

Example 1

Assays on Pure Viral DNAs

The HRE7-PCR assay was firstly performed on serial dilutions of plasmid DNA of various HPV types including the hrHPV types 16, 18, 31, 33, 35, 39, 45, 51, 52, 56, 58, 59, 66, 67 and 68, and HPV 6, 11, 26, 34, 40, 42, 43, 44, 53, 54, 55, 57, and 61 in a background of 100 ng human placental DNA. The PCR reaction mixtures of 50 µl contained 1.5 mM $MgCl_2$, 200 µM of each dNTP, 20 pmol of each primer, 1 unit AmpliTaq Gold DNA polymerase (Perkin-Elmer, Foster City, Calif.), and 10 µl of target DNA in Taq Gold buffer (Perkin-Elmer, Foster City, Calif.). 40 PCR cycles were performed using a PE 9700 thermocycler (Perkin-Elmer, Foster City, Calif.). Each PCR reaction was initiated by a preheating step for 6 minutes at 94° C. followed by 40 cycles consisting of a denaturation step (30 seconds at 94° C.), a primer annealing step (60 seconds at 60° C.), and an elongation step (60 seconds at 72° C.). Ramping times were as described previously (van den Brule et al., 2002, J. Clin. Microbiol. 40, 779-787). The final elongation step was extended for 4 minutes.

All 15 hrHPV clones revealed a clear amplification signal as determined by EIA read-out, whereas no cross-reactivity was observed with human DNA or other HPV types such as HPV 6, 11, 26, 34, 40, 42, 43, 44, 53, 54, 55, 57, and 61. This indicates a high specificity. The dilution lines of cloned HPVs 16, 18, 31, 33, 35, 39, 45, 51, 52, 56, 58, 59, 67 and 68 mixed with human placental DNA revealed an analytical sensitivity ranging from 10 fg to 100 fg plasmid DNA, which corresponds to about 200 to 2,000 viral copies per test. This contradicts the performance of a published hrHPV multiplex PCR assay targeting the E7 region, which was far more sensitive by detecting about 10 viral copies per test (Gheit et al., J Clin Microbiol. 2006:44:2025-2031). As a consequence the latter assays detected a higher number of hrHPV infections, including multiple infections, than GP5+/6+-PCR (Gheit et al., J Clin Microbiol. 2006:44:2025-2031). Also RLB typing revealed specific signals without cross-reactivity and the sensitivity was in the same range as that of the EIA.

Example 2

Pilot Study on Tissue Samples

In a pilot experiment the application of the HRE7-PCR assay was initiated on a series of cervical carcinoma specimens both of the squamous and adenocarcinoma histotype that earlier were tested by GP5+/6+-PCR. These include samples that scored negative by L1-based GP5+/6+-PCR, but positive by E6/E7 type-specific PCR for one or more hrHPV types (Walboomers et al., J Pathol 1999:189:12-19; Zielinski et al., J Pathol 2003:201:535-543). The latter finding is suggestive of viral DNA integration with interruption of the L1 region where the GP5+ and GP6+ primer binding sequences reside. The HRE7-PCR assay so far did not only confirm the positivity obtained by GP5+/6+-PCR, but also scored 25 samples positive that were GP5+/6+-PCR negative, but E6/E7 type-specific PCR positive. On the basis of these pilot data it can be anticipated that compared to E1 or L1-based PCR assays, HRE7-PCR can detect at least 5% more cervical carcinomas.

Example 3

Analysis of Cervical Scrapings in Cohort Studies

For the analysis of the performance of the HRE7-PCR assay on cervical scrapings, we studied larger series of cervical scrapings collected during the course of various population-based cervical screening trials, such as the POBASCAM (Bulkmans et al., Int J Cancer 2004:110:94-101) trial. The cervical scrapings included a total of 56 scrapings of women with 3 and 300 of women with repeat normal cytology in a 5 years interval participating in the POBASCAM trial. A further analysis involved a series of 35 cervical scrapings that were negative by the standard GP5+/6+-PCR performed on crude extracts of women with CIN 3 selected from almost 1,500 women with prevalent/incident CIN 3 in various cohorts. HRE7 PCR was performed on isolated DNA whereas GP5+/6+-PCR was performed on both crude extracts (classic GP5+/6+-PCR method; GP5+/6+-PCR (crude)) and isolated DNA (GP5+/6+-PCR (isolate)).

GP5+/6+-PCR (crude), GP5+/6+-PCR (isolate) and HRE7-PCR revealed a positive test result for all 56 (100%) cervical scrapes of the POBASCAM women with 3. The positivity rate for normal samples was 11/300 (3.7%, 95%

CI:1.6-5.9) for GP5+/6+-PCR (crude) versus 19/300 (6.3%, 95% CI:3.5-9.1) for HRE7-PCR. GP5+/6+-PCR (isolate) scored a similar number of normal scrapings positive (i.e. 17/300, 5.6%, 95% CI:3.0-8.2) as HRE7-PCR (P=0.5). Moreover, HRE7-PCR was positive for 25/35 (71%, 95% CI:56-86) GP5+/6+-PCR (crude) negative scrapings of women with ≥CIN3. Although GP5+/6+-PCR (isolate) was positive as well for 14 of the 35 (40%, 95% CI:24-56) scrapings, this positivity rate was still lower than that of HRE7 PCR (P<0.001). For those cases that score HRE7-PCR positive, but GP5+/6+-PCR negative viral integration will be verified by the APOT assay (Klaes et al., Cancer Res. 1999, 15; 59:6132-6136).

Example 4

Comparison of High-Risk HPV Genotyping by HRE7 PCR and GP5+/6+-PCR Using Reverse Line Blotting All PCR products of samples detailed in Example 3 that were positive in both. HRE7-PCR and GP5+/6+-PCR were subjected to genotyping using the RLB methods linked to both PCR assays. For these cases the agreement for genotyping one or more of the 15 hrHPV types detectable by both assays was 100% (Kappa=1.0).

The invention claimed is:

1. A method to assess the risk of cervical cancer in a female subject which method comprises detecting the presence of one or more hrHPV types, selected from the group consisting of HPV type 16, 18, 31, 33, 35, 39, 45, 51, 52, 56, 58, 59, 66, 67 and 68 in a cervical sample from said subject comprising the steps of:
  (a) providing a sample suspected of harbouring said hrHPVs;
  (b) providing a plurality of forward and backward primers collectively substantially complementary to DNA of all of said hrHPVs wherein said plurality of primers comprises all the primers of SEQ ID NOS:1-15;
  (c) performing under conditions of reduced stringency a reaction to amplify DNA derived from the said sample using said plurality of primers; and
  (d) detecting DNA amplification products from one or more of said hrHPVs from said sample by hybridising the reaction products of the said DNA amplification reaction to a plurality of hrHPV probes which plurality contains probes specifically complementary to the nucleic acid sequence of the said DNA amplification product from each hrHPV type 16, 18, 31, 33, 35, 39, 45, 51, 52, 56, 58, 59, 66, 67 and 68 wherein said hrHPV probes comprise all the probes of SEQ ID NOS:16-30 or all of the probes of SEQ ID NOS:31-45;
wherein said method is effective to detect each and every one of said types if each said type is present, wherein the presence of one or more said hrHPV types indicates said subject to be at risk for cervical cancer.

2. The method of claim 1 wherein all the forward or all the backward primers of said plurality of primers comprise a biotin label.

3. The method of claim 1 wherein said probes comprise a DIG label.

* * * * *